United States Patent
Molaei et al.

(10) Patent No.: US 8,632,580 B2
(45) Date of Patent: Jan. 21, 2014

(54) FLEXIBLE MEDICAL DEVICES INCLUDING METALLIC FILMS

(75) Inventors: Masoud Molaei, Fremont, CA (US); Alexander Leynov, Walnut Creek, CA (US); Robert Z. Obara, Fremont, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1410 days.

(21) Appl. No.: 11/025,158

(22) Filed: Dec. 29, 2004

(65) Prior Publication Data
US 2006/0142845 A1    Jun. 29, 2006

(51) Int. Cl.
*A61F 2/06*      (2013.01)
(52) U.S. Cl.
USPC ......... 623/1.13; 623/1.11; 623/1.18; 623/1.2; 623/1.22; 623/1.34; 623/1.39
(58) Field of Classification Search
USPC ........... 623/1.22, 1.53, 1.39, 1.13, 1.15–1.16, 623/1.18–1.19, 1.32, 1.51
See application file for complete search history.

(56) References Cited

U.S. PATENT DOCUMENTS

| | | |
|---|---|---|
| 4,793,348 A | 12/1988 | Palmaz |
| 4,864,824 A | 9/1989 | Gabriel et al. |
| 5,035,706 A | 7/1991 | Giantureo et al. |
| 5,061,914 A | 10/1991 | Busch et al. |
| 5,085,535 A | 2/1992 | Solberg et al. |
| 5,119,555 A | 6/1992 | Johnson |
| 5,245,738 A | 9/1993 | Johnson |
| 5,302,261 A | 4/1994 | LeRoy et al. |
| 5,306,294 A | 4/1994 | Winston et al. |
| 5,325,880 A | 7/1994 | Johnson et al. |
| 5,382,261 A | 1/1995 | Palmaz |
| 5,405,378 A | 4/1995 | Strecker et al. |
| 5,441,515 A | 8/1995 | Khosravi et al. |
| 5,518,680 A | 5/1996 | Cima et al. |
| 5,554,182 A | 9/1996 | Dinh et al. |
| 5,556,413 A | 9/1996 | Lam |
| 5,607,466 A | 3/1997 | Imbert et al. |

(Continued)

FOREIGN PATENT DOCUMENTS

| | | |
|---|---|---|
| EP | 0472731 | 8/1991 |
| EP | 0 792 627 A2 | 9/1997 |

(Continued)

OTHER PUBLICATIONS

International Search Report for PCT Application No. PCT/US2005/006993.

(Continued)

*Primary Examiner* — David Isabella
*Assistant Examiner* — Jacqueline Woznicki
(74) *Attorney, Agent, or Firm* — Bingham McCutchen LLP

(57) ABSTRACT

Medical devices, such as endoprostheses, and methods of making the devices are disclosed. The medical device can include a stent body and a cover including a deposited metallic film. The medical device can be delivered using a delivery device along a tortuous body passage to a treatment site without damaging the medical device, delivery device, or the body passage. In some cases, the stent body is a flexible helical stent body, which may be threaded through one or more fenestrations of the cover. The cover may include longitudinally extending slits or seams, which help the cover to pass through small radii passages without buckling.

9 Claims, 7 Drawing Sheets

(56) References Cited

U.S. PATENT DOCUMENTS

| | | | |
|---|---|---|---|
| 5,619,177 A | 4/1997 | Johnson et al. | |
| 5,656,036 A | 8/1997 | Palmaz | |
| 5,667,523 A | 9/1997 | Bynon et al. | |
| 5,674,242 A | 10/1997 | Phan et al. | |
| 5,676,697 A | 10/1997 | McDonald | |
| 5,728,150 A | 3/1998 | McDonald et al. | |
| 5,733,326 A * | 3/1998 | Tomonto et al. | 623/1.44 |
| 5,755,734 A | 5/1998 | Richter et al. | |
| 5,800,517 A | 9/1998 | Anderson et al. | |
| 5,817,102 A | 10/1998 | Johnson et al. | |
| 5,824,042 A | 10/1998 | Lombardi et al. | |
| 5,824,049 A | 10/1998 | Ragheb et al. | |
| 5,824,054 A | 10/1998 | Khosravi et al. | |
| RE35,988 E | 12/1998 | Winston et al. | |
| 5,843,158 A | 12/1998 | Lenker et al. | |
| 5,843,164 A | 12/1998 | Frantzen et al. | |
| 5,843,289 A | 12/1998 | Lee et al. | |
| 5,849,206 A | 12/1998 | Amon et al. | |
| 5,860,998 A | 1/1999 | Robinson et al. | |
| 5,865,723 A | 2/1999 | Love et al. | |
| 5,882,444 A | 3/1999 | Flomenblit et al. | |
| 5,888,734 A | 3/1999 | Cremer et al. | |
| 5,897,911 A | 4/1999 | Loeffler | |
| 5,903,099 A | 5/1999 | Johnson et al. | |
| 5,938,697 A | 8/1999 | Killion et al. | |
| 5,941,249 A | 8/1999 | Maynard | |
| 5,957,929 A | 9/1999 | Brenneman | |
| 5,984,963 A | 11/1999 | Ryan et al. | |
| 6,007,573 A | 12/1999 | Wallace et al. | |
| 6,015,431 A | 1/2000 | Thornton et al. | |
| 6,015,433 A | 1/2000 | Roth | |
| 6,017,977 A | 1/2000 | Evans et al. | |
| 6,036,725 A | 3/2000 | Avellanet | |
| 6,043,451 A | 3/2000 | Julien et al. | |
| 6,048,622 A | 4/2000 | Hagood et al. | |
| 6,059,766 A | 5/2000 | Greff | |
| 6,077,298 A | 6/2000 | Tu et al. | |
| 6,096,175 A | 8/2000 | Roth | |
| 6,099,561 A | 8/2000 | Alt | |
| 6,107,004 A | 8/2000 | Donadio, III | |
| 6,120,535 A | 9/2000 | McDonald et al. | |
| 6,132,460 A | 10/2000 | Thompson | |
| 6,133,547 A | 10/2000 | Maynard | |
| 6,139,564 A | 10/2000 | Teoh | |
| 6,143,022 A * | 11/2000 | Shull et al. | 623/1.13 |
| 6,159,239 A * | 12/2000 | Greenhalgh | 623/1.13 |
| 6,174,330 B1 | 1/2001 | Stinson | |
| 6,190,404 B1 | 2/2001 | Palmaz et al. | |
| 6,206,911 B1 | 3/2001 | Milo | |
| 6,224,627 B1 | 5/2001 | Armstrong et al. | |
| 6,224,630 B1 | 5/2001 | Bao et al. | |
| 6,245,104 B1 | 6/2001 | Alt | |
| 6,254,628 B1 | 7/2001 | Wallace et al. | |
| 6,258,117 B1 | 7/2001 | Camrud et al. | |
| 6,290,720 B1 | 9/2001 | Khosravi et al. | |
| 6,303,100 B1 | 10/2001 | Ricci et al. | |
| 6,315,788 B1 | 11/2001 | Roby | |
| 6,315,794 B1 | 11/2001 | Richter | |
| 6,355,055 B1 | 3/2002 | Waksman et al. | |
| 6,379,383 B1 | 4/2002 | Palmaz et al. | |
| 6,398,803 B1 | 6/2002 | Layne et al. | |
| 6,406,487 B2 | 6/2002 | Brenneman | |
| 6,406,490 B1 | 6/2002 | Roth | |
| 6,409,749 B1 | 6/2002 | Maynard | |
| 6,428,569 B1 | 8/2002 | Brown | |
| 6,447,478 B1 | 9/2002 | Maynard | |
| 6,454,738 B1 | 9/2002 | Tran et al. | |
| 6,458,152 B1 | 10/2002 | Khosravi et al. | |
| 6,458,153 B1 | 10/2002 | Bailey et al. | |
| 6,471,980 B2 | 10/2002 | Sirhan et al. | |
| 6,485,510 B1 | 11/2002 | Camrud et al. | |
| 6,506,211 B1 | 1/2003 | Fleischman et al. | |
| 6,520,984 B1 | 2/2003 | Garrison et al. | |
| 6,527,919 B1 | 3/2003 | Roth | |
| 6,533,905 B2 | 3/2003 | Johnson et al. | |
| 6,537,310 B1 * | 3/2003 | Palmaz et al. | 623/1.13 |
| 6,605,111 B2 | 8/2003 | Bose et al. | |
| 6,614,570 B2 | 9/2003 | Johnson et al. | |
| 6,618,921 B1 | 9/2003 | Thornton | |
| 6,620,192 B1 | 9/2003 | Jalisi | |
| 6,620,634 B2 | 9/2003 | Johnson et al. | |
| 6,624,730 B2 | 9/2003 | Johnson et al. | |
| 6,629,993 B2 | 10/2003 | Voinov | |
| 6,632,240 B2 | 10/2003 | Khosravi et al. | |
| 6,638,301 B1 | 10/2003 | Chandrasekaran et al. | |
| 6,666,882 B1 | 12/2003 | Bose et al. | |
| 6,669,719 B2 | 12/2003 | Wallace et al. | |
| 6,669,721 B1 | 12/2003 | Bose et al. | |
| 6,669,795 B2 | 12/2003 | Johnson et al. | |
| 6,673,102 B1 | 1/2004 | Vonesh et al. | |
| 6,676,987 B2 | 1/2004 | Zhong et al. | |
| 6,695,865 B2 | 2/2004 | Boyle et al. | |
| 6,699,278 B2 | 3/2004 | Fischell et al. | |
| 6,699,279 B2 | 3/2004 | Stevens et al. | |
| 6,746,478 B2 | 6/2004 | Jayaraman | |
| 6,752,826 B2 | 6/2004 | Holloway et al. | |
| 6,767,418 B1 | 7/2004 | Zhang et al. | |
| 6,776,795 B2 | 8/2004 | Pelton | |
| 6,820,676 B2 | 11/2004 | Palmaz et al. | |
| 6,849,085 B2 | 2/2005 | Marton | |
| 6,899,730 B1 * | 5/2005 | Rivelli, Jr. | 623/1.15 |
| 6,936,066 B2 | 8/2005 | Palmaz et al. | |
| 6,953,560 B1 | 10/2005 | Castro et al. | |
| 7,105,018 B1 * | 9/2006 | Yip et al. | 623/1.15 |
| 7,279,175 B2 | 10/2007 | Chen et al. | |
| 7,410,497 B2 | 8/2008 | Hastings et al. | |
| 7,947,071 B2 | 5/2011 | Schmid et al. | |
| 2001/0001834 A1 | 5/2001 | Palmaz et al. | |
| 2001/0032013 A1 | 10/2001 | Marton | |
| 2001/0039449 A1 | 11/2001 | Johnson et al. | |
| 2001/0044647 A1 | 11/2001 | Pinchuk et al. | |
| 2002/0007958 A1 | 1/2002 | Rivelli et al. | |
| 2002/0017503 A1 | 2/2002 | Banas et al. | |
| 2002/0019662 A1 | 2/2002 | Brauckman et al. | |
| 2002/0035774 A1 | 3/2002 | Austin | |
| 2002/0042645 A1 | 4/2002 | Shannon | |
| 2002/0046783 A1 | 4/2002 | Johnson et al. | |
| 2002/0142119 A1 | 10/2002 | Seward et al. | |
| 2002/0151965 A1 | 10/2002 | Roth | |
| 2002/0161342 A1 | 10/2002 | Rivelli, Jr. et al. | |
| 2002/0162605 A1 | 11/2002 | Horton et al. | |
| 2002/0165576 A1 | 11/2002 | Boyle et al. | |
| 2002/0165600 A1 | 11/2002 | Banas et al. | |
| 2002/0173809 A1 | 11/2002 | Fleischman et al. | |
| 2002/0187288 A1 | 12/2002 | Lim et al. | |
| 2002/0193869 A1 | 12/2002 | Dang | |
| 2002/0195579 A1 | 12/2002 | Johnson | |
| 2002/0198584 A1 | 12/2002 | Unsworth et al. | |
| 2003/0002994 A1 | 1/2003 | Johnson et al. | |
| 2003/0004567 A1 | 1/2003 | Boyle et al. | |
| 2003/0018354 A1 | 1/2003 | Roth et al. | |
| 2003/0023303 A1 | 1/2003 | Palmaz et al. | |
| 2003/0040791 A1 | 2/2003 | Oktay | |
| 2003/0050691 A1 | 3/2003 | Shifrin et al. | |
| 2003/0059640 A1 | 3/2003 | Marton et al. | |
| 2003/0060782 A1 | 3/2003 | Bose et al. | |
| 2003/0074049 A1 | 4/2003 | Hoganson et al. | |
| 2003/0078649 A1 | 4/2003 | Camrud et al. | |
| 2003/0083731 A1 | 5/2003 | Kramer et al. | |
| 2003/0127318 A1 | 7/2003 | Johnson et al. | |
| 2003/0130718 A1 | 7/2003 | Palmas et al. | |
| 2003/0130721 A1 * | 7/2003 | Martin et al. | 623/1.13 |
| 2003/0139797 A1 | 7/2003 | Johnson et al. | |
| 2003/0153971 A1 | 8/2003 | Chandrasekaran | |
| 2003/0159920 A1 | 8/2003 | Roth | |
| 2003/0185895 A1 | 10/2003 | Lanphere et al. | |
| 2003/0187495 A1 | 10/2003 | Cully et al. | |
| 2003/0212430 A1 | 11/2003 | Bose et al. | |
| 2004/0006381 A1 | 1/2004 | Sequin et al. | |
| 2004/0014253 A1 | 1/2004 | Gupta et al. | |
| 2004/0030377 A1 | 2/2004 | Dubson et al. | |
| 2004/0034408 A1 | 2/2004 | Majercak et al. | |
| 2004/0054399 A1 | 3/2004 | Roth | |
| 2004/0054406 A1 | 3/2004 | Dubson et al. | |

(56) References Cited

U.S. PATENT DOCUMENTS

| | | |
|---|---|---|
| 2004/0059410 A1* | 3/2004 | Cox .............................. 623/1.19 |
| 2004/0098095 A1 | 5/2004 | Burnside et al. |
| 2004/0107004 A1 | 6/2004 | Levine et al. |
| 2004/0143317 A1 | 7/2004 | Stinson et al. |
| 2004/0186556 A1* | 9/2004 | Hogendijk et al. .......... 623/1.16 |
| 2004/0199239 A1 | 10/2004 | Austin et al. |
| 2004/0225350 A1 | 11/2004 | Shanley |
| 2004/0254520 A1 | 12/2004 | Porteous et al. |
| 2005/0004653 A1 | 1/2005 | Gerberding et al. |
| 2005/0010275 A1 | 1/2005 | Sahatjian et al. |
| 2005/0033399 A1 | 2/2005 | Richter |
| 2005/0165468 A1 | 7/2005 | Marton |
| 2005/0165469 A1 | 7/2005 | Hogendijk |
| 2005/0197687 A1 | 9/2005 | Molaei et al. |
| 2005/0197689 A1 | 9/2005 | Molaei et al. |
| 2005/0197690 A1* | 9/2005 | Molaei et al. ................ 623/1.13 |
| 2005/0222667 A1* | 10/2005 | Hunt ............................ 623/1.13 |
| 2006/0069428 A1* | 3/2006 | Feller ........................... 623/1.44 |
| 2006/0100659 A1 | 5/2006 | Dinh et al. |
| 2006/0115514 A1 | 6/2006 | Gengrinovitch |
| 2006/0122691 A1 | 6/2006 | Richter |
| 2006/0142838 A1 | 6/2006 | Molaei et al. |
| 2006/0142842 A1 | 6/2006 | Molaei et al. |
| 2006/0142845 A1 | 6/2006 | Molaei et al. |
| 2006/0142851 A1 | 6/2006 | Molaei et al. |
| 2006/0147492 A1 | 7/2006 | Hunter et al. |
| 2006/0184231 A1 | 8/2006 | Rucker |
| 2006/0259131 A1 | 11/2006 | Molaei et al. |
| 2006/0271158 A1 | 11/2006 | Olson |
| 2007/0016283 A1 | 1/2007 | Greenhalgh et al. |
| 2007/0073385 A1 | 3/2007 | Schaeffer et al. |
| 2007/0112411 A1 | 5/2007 | Obermiller et al. |
| 2007/0250156 A1 | 10/2007 | Palmaz |
| 2008/0027388 A1 | 1/2008 | Banas et al. |
| 2008/0221665 A1 | 9/2008 | Peckham et al. |
| 2009/0132022 A1 | 5/2009 | Banas |
| 2009/0187240 A1 | 7/2009 | Clerc et al. |
| 2010/0030320 A1 | 2/2010 | Feller, III |
| 2011/0054590 A1 | 3/2011 | Leopold et al. |

FOREIGN PATENT DOCUMENTS

| | | |
|---|---|---|
| EP | 1 604 697 | 12/2005 |
| EP | 1 725 186 | 11/2006 |
| EP | 1 725 187 | 11/2006 |
| EP | 1 725 188 | 11/2006 |
| GB | 2 125 442 A | 3/1994 |
| JP | 2003-102849 | 8/2003 |
| JP | 2007/502069 | 9/2007 |
| JP | 2007/526098 | 9/2007 |
| JP | 2007/526099 | 9/2007 |
| WO | WO 96/06814 | 3/1996 |
| WO | WO 98/53362 | 11/1998 |
| WO | WO 99/02092 | 1/1999 |
| WO | WO 99/60267 | 12/1999 |
| WO | WO 99/62432 | 12/1999 |
| WO | WO 00/62711 | 10/2000 |
| WO | WO 01/21097 | 3/2001 |
| WO | WO 01/53559 | 7/2001 |
| WO | WO 01/87371 | 11/2001 |
| WO | WO 01/89420 | 11/2001 |
| WO | 01/95697 | 12/2001 |
| WO | WO 01/91823 | 12/2001 |
| WO | WO 02/34163 | 5/2002 |
| WO | WO 02/38080 | 5/2002 |
| WO | WO 02/38086 | 5/2002 |
| WO | WO 02/060506 | 8/2002 |
| WO | WO 03/003943 | 1/2003 |
| WO | WO 03/011363 | 2/2003 |
| WO | WO 03/013337 | 2/2003 |
| WO | WO 03/015840 | 2/2003 |
| WO | WO 03/018100 | 3/2003 |
| WO | WO 03/075793 | 9/2003 |
| WO | WO 03/075799 A1 | 9/2003 |
| WO | 03/099161 A2 | 12/2003 |
| WO | WO 2004/002370 A1 | 1/2004 |
| WO | WO 2004/008504 | 1/2004 |
| WO | WO 2004/028340 | 4/2004 |
| WO | 2005/084583 | 9/2005 |
| WO | 2005/084584 | 9/2005 |
| WO | 2005/084585 | 9/2005 |
| WO | 2006/125022 | 4/2006 |
| WO | 2006/071215 | 7/2006 |
| WO | 2006/071242 | 7/2006 |
| WO | 2006/071243 | 7/2006 |
| WO | 2006/071244 | 7/2006 |
| WO | WO 2006/071245 | 7/2006 |

OTHER PUBLICATIONS

International Search Report for PCT Application No. PCT/US2005/007161.

International Search Report for PCT Application No. PCT/US2005/007173.

International Search Report for PCT Application No. PCT/US2005/006895.

International Search Report for PCT Application No. PCT/US2005/007162.

Dieter, George, *Mechanical Metallurgy*, Singapore, McGraw-Hill Book Co., $10^{th}$ Printing 1984, pp. 111-117, 142-145, and 234-237. TA405.D53.

Freiherr, Greg, "Shape-Memory Alloys Offer Untapped", Medical Device & Diagnostic Industry Magazine, Mar. 1998, 5 pages [retrieved on Jun. 30, 2004].

Fu et al., "TiNi-based thin films in MEMS applications: a review", Sensors and Actuators, Article in Press, Elsevier, Feb. 2004, 14 pages.

Gertner et al., "Drug Delivery from Electrochemically Deposited Thin Metal Films", Electrochemical and Sold-State Letter, 6 (4) J4-J6, 2003.

Gertner et al., "Electrochemistry and Medical Devices: Friend or Foe?", The Electrochemical Society Interface, Fall 2003, pp. 20-24.

Gupta et al., "Nitinol Thin Film Three-Dimensional Devices—Fabrication and Applications", http://www.tinialloy.com/pdf/smst.pdf, Sep. 7, 2003 [retrieved Dec. 1, 2004].

He et al., "$CO_2$ laser annealing of sputtering deposited NiTi shape memory thin films", Journal of Micromechanics and Microengineering, May 20, 2004, pp. 950-956.

Kaczmarek, S. M., "Pulsed laser deposition—today and tomorrow", STL'96, Proc. SPIE, vol. 3187, 1997, pp. 129-134.

Krebs et al., "Pulsed Laser Deposition (PLD)—a Versatile Thin Film Technique", Advances in Solid State Physics 2003, 43, 505-517.

Nakayama et al., "Fabrication of micropored elastomeric film-covered stents and acute-phase performances", Journal of Biomedical Mateirals Research Part A, vol. 64A, Issue 1, Sep. 30, 2002, pp. 52-61.

Neocera, Inc. Brochure—Pulsed Laser Deposition, www.neocera.com [retrieved Dec. 1, 2004].

Pelleiter et al., "Effect of high energy argon implantation into NiTi shape memory alloy", Surface and Coatings Technology, 158-159, 2002, pp. 301-308.

Padhi et al., "Planarization of Copper Thin Films by Electropolishing in Phosphoric Acid for ULSI Application", Journal of Electrochemical Society, vol. 150, 2003, pp. G10-G14.

Ren et al., "Carbon nitride materials synthesized by Ion-assisted pulsed laser deposition", RIKEN Review No. 43, Jan. 2002, pp. 41-44.

Schetky et al., "Issues in the Further Development of Nitinol Properties and Processing for Medical Device Application", Proceedings, ASM Materials & Processes for Medical Devices Conference, Anaheim, in press, 2003, 6 pages.

Shabalovskaya et al., "Comparative performances of Nitinol surfaces in protein adsorption and platelet adhesion—Preliminary results", Institute for Physical Research and Technology, Ames Laboratory, Ames, IA University of Washington, Seattle WA Memry Corporation, Bethel CT, 2004, 10 pages.

(56) References Cited

OTHER PUBLICATIONS

Stoeckel et al., "A survey of stent designs", Min Invas Ther & Allied Technol, 11(4), 2002, pp. 137-147.
International Search Report from European Patent Application No. PCT/US2005/007282 mailed Jul. 5, 2005, 15 pages.
International Search Report from European Patent Application No. PCT/US2005/007164 mailed Jul. 5, 2005, 13 pages.
International Search Report from European Patent Application No. PCT/US2006/019126 mailed Feb. 1, 2007, 16 pages.

* cited by examiner

FLEXIBLE MEDICAL DEVICES INCLUDING METALLIC FILMS

FIELD OF THE INVENTION

The invention relates to medical devices, such as endoprostheses, and methods of making the devices.

BACKGROUND

The body includes various passageways such as arteries, other blood vessels, and other body lumens. These passageways sometimes become occluded or weakened. For example, the passageways can be occluded by a tumor, restricted by plaque, or weakened by an aneurysm. When this occurs, the passageway can be reopened or reinforced, or even replaced, with a medical endoprosthesis. An endoprosthesis is typically a tubular member that is placed in a lumen in the body. Endoprostheses can be delivered inside the body by a catheter that supports the endoprosthesis in a compacted or reduced-size form as the endoprosthesis is transported to a desired site. Upon reaching the site, the endoprosthesis is expanded, for example, so that it can contact the walls of the lumen.

The expansion mechanism may include forcing the endoprosthesis to expand radially. For example, the expansion mechanism can include the catheter carrying a balloon, which carries a balloon-expandable endoprosthesis. The balloon can be inflated to deform and to fix the expanded endoprosthesis at a predetermined position in contact with the lumen wall. The balloon can then be deflated, and the catheter withdrawn.

In another delivery technique, the endoprosthesis is formed of an elastic material that can be reversibly compacted and expanded, e.g., elastically or through a material phase transition. During introduction into the body, the endoprosthesis is restrained in a radially compacted condition. Upon reaching the desired implantation site, the restraint is removed, for example, by retracting a restraining device such as an outer sheath, enabling the endoprosthesis to self-expand by its own internal elastic restoring force.

SUMMARY OF THE INVENTION

The invention relates to medical devices, such as endoprostheses, and methods of making the devices. Exemplary endoprostheses include stents, covered stents, and stent-grafts.

In some embodiments, an endoprosthesis includes a generally tubular framework having at least one helical member and a deposited metallic film having a thickness of less than about 50 µm. The deposited metallic film may be concentric with the tubular framework.

The deposited metallic film may include, e.g., deposited nickel and titanium. The deposited film may have a thickness of about 50 µm or less, 50 µm or less, e.g., about 35 µm or less. The deposited film may have a thickness of 4 µm or greater. The film may exhibit super-elastic properties.

The tubular framework and the metallic film may be secured together at substantially only one distance from an end of the endoprosthesis.

The metallic film may include at least one fenestration, with the helical member passing through the fenestration so that a first portion of the helical member is internal to the cover and a second portion of the helical member is external to the cover. The metallic film may include a plurality of fenestrations spaced apart along a length of the endoprosthesis. The helical member may pass through each of the fenestrations.

At least 2/3 of a length of the helical member may be internal to the cover.

In some embodiments, an endoprosthesis includes a generally tubular framework and a cover comprising at least one metallic film defining a thickness of about 50 µm or less. The cover may be concentric with the framework. The cover may define a length and a plurality of slits. Each slit may extend generally along a longitudinal axis of the endoprosthesis. A length of each slit may be at least about 30% as long as the length of the cover.

The metallic film may be a deposited metallic film including, e.g., deposited nickel and titanium. The deposited film may have a thickness of about 50 µm or less, 50 µm or less, e.g., about 35 µm or less. The deposited film may have a thickness of 4 µm or greater. The film may exhibit super-elastic properties.

The cover may include a plurality of cover portions. Each cover portion may include a respective a metallic film defining a thickness of about 50 µm or less. Each cover portion may have a cross-section perpendicular to the longitudinal axis that defines less than a complete circumference while a cross section of the cover perpendicular to the longitudinal axis defines an essentially complete circumference.

Each metallic film may be a deposited metallic film including deposited nickel and titanium.

At least some of the slits may extend for less than 80% of the length of the cover.

The generally tubular framework may include or consist of a helical member.

In some embodiments, an endoprosthesis includes a generally tubular metallic film having first and second end portions and a central portion. The metallic film of the central portion may have a thickness of less than about 25 µm. The metallic film of the end portions may have a thickness greater than the central portion and less than about 50 µm.

The film may be a deposited metallic film including, e.g., deposited nickel and titanium. The deposited film may have a thickness of about 50 µm or less, 50 µm or less, e.g., about 35 µm or less. The deposited film may have a thickness of 4 µm or greater. The film may exhibit super-elastic properties.

The thickness of at least one of the end portions may be at least 3 times greater than the thickness of the central portion. The end portions may be configured to exert an outward radial force against body passage. The outward radial force may be sufficient to maintain a position of the endoprosthesis.

Each of the end portions and the central portion may have a respective length. The length of each end portion may be at least 10% of the length of the central portion.

In some embodiments, an endoprosthesis defines a longitudinal axis and is configured to have a radially compacted state within a delivery device and a radially expanded state when deployed within a body passage. The endoprosthesis may include a generally tubular metallic film defining a thickness of about 50 µm or less. The metallic film may include a plurality of first apertures and a plurality of second apertures. Each of the first and second apertures may be oriented generally perpendicular to one another. Each first aperture may be configured to (a) define an opening when the catheter is in the radial compacted state and (b) define a slit when the catheter is in the radially expanded state. Each second aperture may be configured to (a) define a slit when the catheter is in the radial compacted state and (b) define an opening when the catheter is in the radially expanded state.

The film may be a deposited metallic film including, e.g., deposited nickel and titanium. The deposited film may have a thickness of about 50 μm or less, 50 μm or less, e.g., about 35 μm or less. The deposited film may have a thickness of 4 μm or greater. The film may exhibit super-elastic properties.

The metallic film may define a plurality of sets of apertures. Each set of apertures may include (a) at least one of the first apertures, (b) at least one of the second apertures, and (c) at least one fenestration, which may define an elongated opening generally aligned with the longitudinal axis when the metallic film is in the radially compacted state and an elongated opening generally perpendicular to the longitudinal axis when the metallic film is in the radially expanded state. Each set of apertures may include at least two of the first apertures and at least two of the second apertures. The at least two first apertures of each set may be spaced apart by the fenestration of the set and the at least two second apertures of each set may be spaced apart by the fenestration of the set.

The endoprosthesis may include a stent body, with the metallic film and stent body optionally disposed generally concentrically with respect to one another.

In one aspect, the invention features an endoprosthesis including a metallic film, e.g., a vapor deposited film, including nickel, titanium, and chromium. A ratio of a weight of chromium of the metallic film to a combined weight of nickel, titanium, and chromium of the metallic film is at least 0.001 and can be less than 0.0075.

Other aspects, features, and advantages of the invention will be apparent from the description of the preferred embodiments thereof and from the claims.

BRIEF DESCRIPTION OF THE FIGURES

FIG. 4b is a cross-sectional view of the endoprosthesis of FIG. 4a.

DETAILED DESCRIPTION

Figure 1:
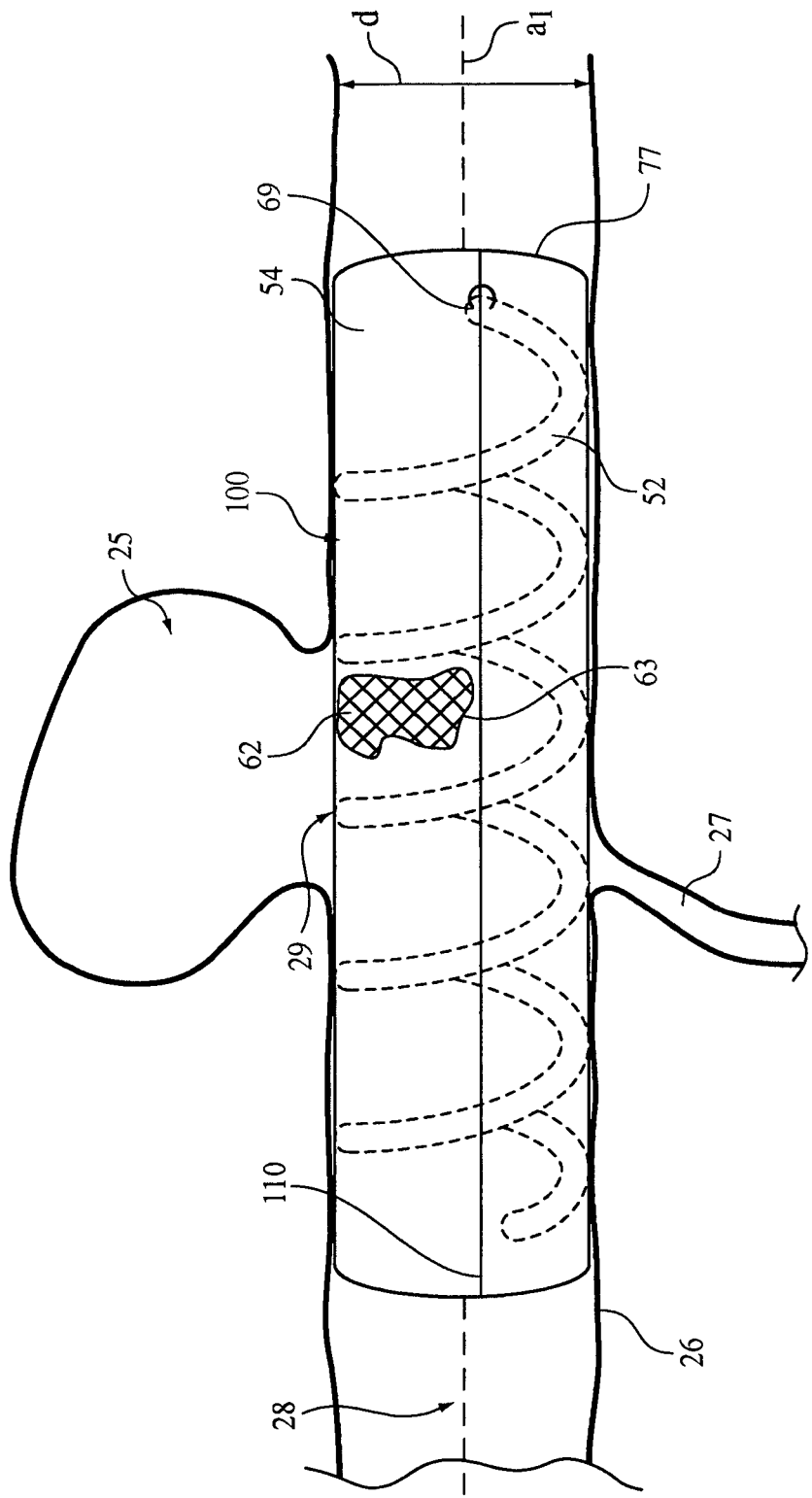
FIG. 1 is a side view of an endoprosthesis in the radially expanded state as deployed within a body passage adjacent an aneurysm.

Referring to FIG. 1, an endoprosthesis 100 is deployed within a body passage, e.g., within a vessel 28 weakened by an aneurysm 25 of a vessel wall 26 of a human brain. Endoprosthesis 100 includes a flexible framework, e.g., a mesh stent body or a helical stent body 52, covered by a tubular member or cover 54. The stent body provides a framework that helps maintain the generally tubular shape of the cover. The framework 52 is coil-like and defines relatively large openings or fenestrations along its length. The cover 54 includes a relatively thin and flexible metallic film having smaller fenestrations 62 than the stent body. For clarity, fenestrations 62, which may cover only one or more portions or all of the cover 54, are shown only within an illustrative portion 63.

The endoprosthesis 100 modifies an amount or velocity of blood passing between vessel 26 and aneurysm 25. For example, prosthesis 100 can be deployed to reduce or block blood flow between vessel 26 and aneurysm 25. If so deployed, prosthesis 100 may sufficiently reduce blood flow to allow clotting or other healing processes to take place within aneurysm 25 and/or opening 29. Tubular member 54 can provide a greater attenuation of the blood flow into the aneurysm 25 than stent body 52 alone. Endoprosthesis 100, however, can allow some flow to pass between vessel 26 and aneurysm 25 even while providing some reduction in the rate and/or volume of flow. Prosthesis 100 can also (or alternatively) allow blood to pass between vessel 26 containing the prosthesis and adjacent vessels, e.g., a feeder vessel 27, while still providing reduced flow with respect to the aneurysm.

Figure 2A:
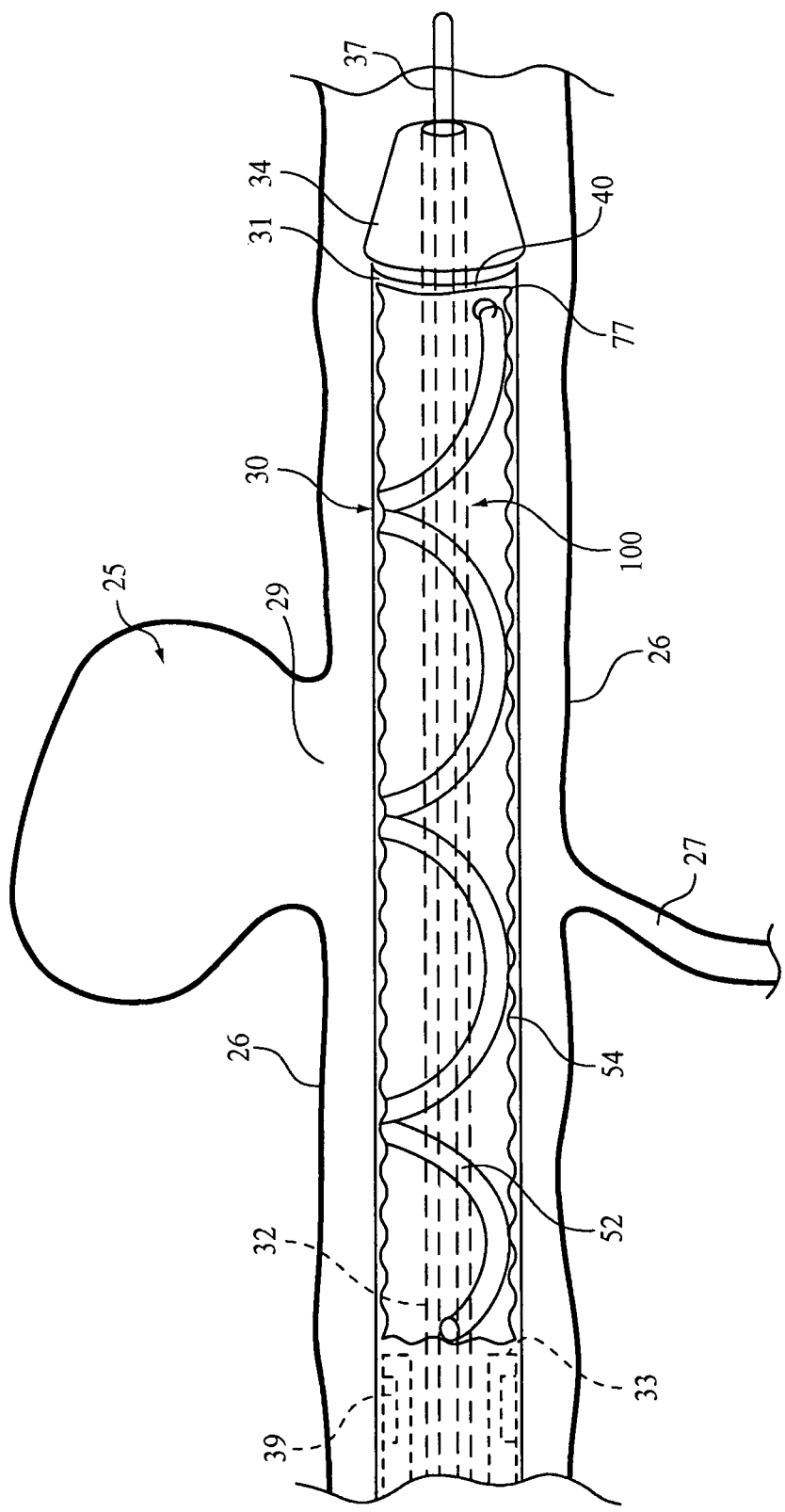
FIG. 2a is a side view of a distal portion of a deployment device prior to radial expansion of the endoprosthesis.
Figure 2B:
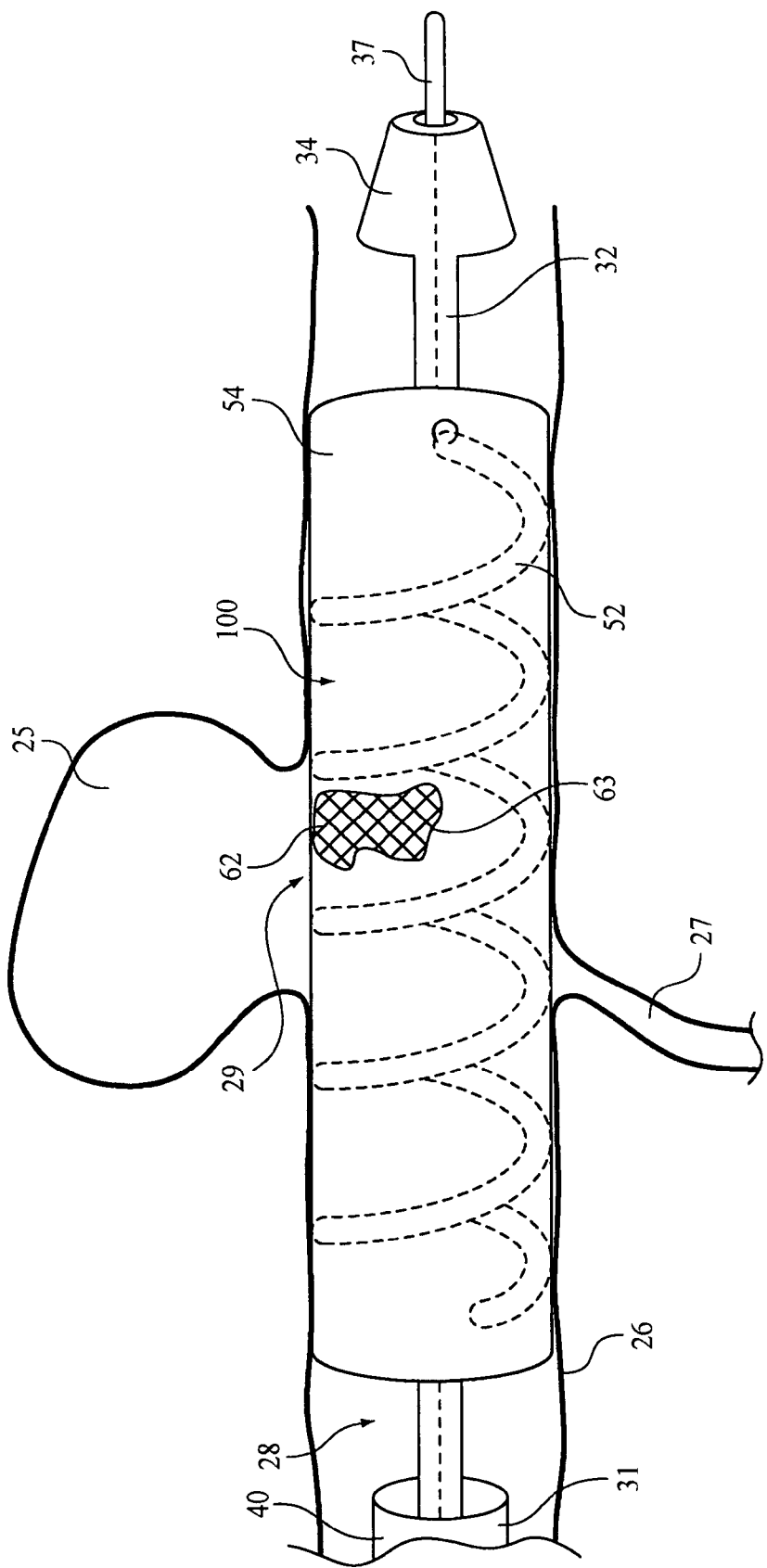
FIG. 2b is a side view of the distal portion of the deployment device subsequent to radial expansion of the endoprosthesis adjacent the aneurysm.

Referring to FIGS. 2a and 2b, endoprosthesis 100 is deployed to aneurysm 25 using a deployment device 30, which includes a retractable outer sheath 31 and an inner catheter 32. FIG. 2a shows only a distal portion of the delivery device. Endoprosthesis 100 is radially compacted between the outer sheath 31 and inner catheter 32 adjacent a distal end 40 of the outer sheath. A proximal stop 33 and a distal tip 34 longitudinally restrain the endoprosthesis during deployment. An operator manipulates the device 30 using a proximal portion (not shown). The radially compacted endoprosthesis is introduced over a guide wire 37 extending along a potentially tortuous pathway between an entry point to the patient's vascular system and aneurysm 25. For example, reaching aneurysms within certain locations within a brain may require navigating device 30 around a small radius curve within a vessel encapsulated by the petrius bone.

The progress of device 30 to a treatment site can be radiographically monitored by markers 39. Prosthesis 100 can include markers, to provide radiopacity, which can also or alternatively be used to visualize the position of endoprosthesis 100. With reference to FIG. 2b, the outer sheath 31 is retracted upon reaching the desired deployment site, e.g., aneurysm 25. In some embodiments, endoprosthesis 100 self-expands radially by its own internal elastic restoring force when the outer sheath is retracted. The expanded prosthesis may maintain the deployed position by exerting an outward radial force against an inner wall of the vessel. Alternatively, or in combination with self-expansion, deployment of prosthesis 100 may include use of a balloon or other device to radially expand prosthesis 100 within vessel 26. The inner catheter 32 and guide wire 37 are withdrawn from vessel 26. Suitable delivery systems include the Neuroform, Neuroform2, and Wingspan Stent System available from Boston Scientific Target Therapeutics, Fremont, Calif. In embodiments, the outer sheath and/or inner catheter includes a reinforcing member to respectively resist elongation or compression as the outer sheath is withdrawn. Such reinforcing members include polymer shafts, braids, and coil structures.

Upon expansion, endoprosthesis 100 assumes a shape and radial extent generally coextensive with an inner surface of the vessel 26, e.g., a tubular shape centered about a longitudinal axis $a_1$ of the prosthesis (FIG. 1). Depending upon the application, prosthesis 100 can have a diameter d of between, for example, 1 mm to 46 mm. In certain embodiments, a prosthesis for deployment within a vessel at an aneurysm can have an expanded diameter d of from about 2 mm to about 6 mm, e.g., about 2.5 mm to about 4.5 mm. Depending upon the application, prosthesis 100 can have a length along axis $a_1$ of at least 5 mm, at least 10 mm, e.g., at least about 30 mm. An exemplary embodiment has an expanded diameter of about 3.5 mm and a length of about 15 mm. In embodiments, the stent body has a closed cell framework, an open cell framework, a helical framework, a braided framework, or combination thereof.

The cover and stent body can be relatively secured by, e.g. fasteners. Attachment techniques include brazing, welding or attachment with a filament, rivets or grommets, or crimping, or adhesive. In some embodiments, the tubular member differs from a fabric at least in that the tubular member lacks fibers than can be pushed apart to receive a filament as in sewing a fabric. Accordingly, the fenestrations used for securing can be formed prior to the process of passing the filament through the tubular member. Fenestrations that receive the filaments can be formed by, e.g., etching, laser cutting, or a photolithographic process. Attachment techniques are described in U.S. Ser. No. 11/025,866 filed contemporaneously herewith and incorporated herein by reference.

The cover is formed of a thin film that exhibits advantageous properties such as strength, toughness, and flexibility by selection of the composition of the film, processing techniques, and mechanical configuration. For example, in particular embodiments, the film is a vapor-deposited material composed of a nickel-titanium alloy having a strength additive, e.g. chromium. The film has a thickness of about 50 µm or less, e.g. about 4-35 µm, and includes fine fenestrations, which facilitate collapsing the film to small diameter for delivery into the body and expansion at the treatment site, while impeding blood access to the aneurysm. In particular embodiments, the film is processed to modify dislocations, which contribute to strength and toughness of the thin film.

Deposited materials are formed by depositing film constituents from a suspended state, e.g. in a vapor or a vacuum onto a surface. In embodiments, the constituents are suspended, e.g. by bombarding, heating or sputtering a bulk target. The suspended constituents deposit on a substrate to form the film. Deposited films can exhibit highly uniform thickness and microstructure in very thin films, e.g. about 50 µm or less, e.g. 4-35 µm. Deposition techniques include sputter deposition, pulsed laser deposition, ion beam deposition and plasma deposition. Suitable deposition processes are described in Busch et al. U.S. Pat. No. 5,061,914, Bose et al. U.S. Pat. No. 6,605,111, Johnston U.S. Pat. No. 6,533,905, and Gupta et al. U.S. 2004/0014253, the entire contents of all of which are hereby incorporated by reference.

In particular embodiments, the deposited film is an alloy that includes nickel and titanium, and a strength additive or additives, which modify a mechanical property, e.g., a . hardness or elasticity, of the film. In particular embodiments, the film is a tertiary alloy that has substantially no other components besides nickel, titanium, and additive present in an amount greater than 1%, 0.5% or 0.2% or less than 20%, 10%, or 5% by weight of the film. The film may consist essentially of nickel, titanium, and chromium. In embodiments, the deposited film includes between 54 and 57 weight percent nickel with the balance composed essentially of titanium and chromium. In some embodiments, a ratio of a weight of chromium of the film to a combined weight of nickel, titanium, and chromium of the film is at least 0.001, at least 0.002 e.g., at least 0.0025. The ratio of the weight of chromium of the film to the combined weight of chromium, nickel, and titanium of the film can be 0.02 or less, 0.01 or less, e.g., 0.0075 or less. The ratio of the weight of chromium to the combined weight of chromium, nickel, and titanium of the film can be about 0.0025. In embodiments, the alloy exhibits superelastic or pseudo-elastic properties. Superelastic or pseudo-elastic metal alloy, as described, for example, in Schetsky, L. McDonald, "Shape Memory Alloys," Encyclopedia of Chemical Technology (3rd ed.), John Wiley & Sons, 1982, vol. 20. pp. 726-736; and commonly assigned U.S. Ser. No. 10/346,487, filed Jan. 17, 2003.

The ability of endoprosthesis 100 to accommodate radial compaction/expansion is determined in part by mechanical properties of the stent body and cover and their interaction during compaction/expansion. The ability of the device 30 to flexibly navigate tortuous pathways without rupturing the vessel wall is determined in part by the mechanical properties of the radially compacted endoprosthesis. Because of their different constructions, a stent body and cover may behave differently during radial compaction/expansion or passage along tortuous pathways, e.g., in terms of flexing, overall conformation, or length changes. In some embodiments, the stent body and cover accommodate such processes at least somewhat independently of the other. For example, cover 54 and stent body 52 may have an amount of relative circumferential and/or longitudinal freedom so that each can slide relative to the other when compacting/expanding or passing through tortuous paths. In embodiments, cover 54 includes generally longitudinal slits or is formed of different cover portions, which may or may not be directly secured to one another along their lengths. Rather than buckling as might a complete tube when navigating small radius curves, different portions of the cover can act independently to accommodate small radii of curvature. Hence, an endoprosthesis may be almost or at least about as accommodating as a stent body and cover individually. Endoprostheses able to navigate tortuous paths without damage to themselves or to body passages are discussed herein.

Referring back to FIG. 1, cover 54 and stent body 52 are secured together at a distal end 77 of endoprosthesis 100 by a filament 69. Portions of cover 54 and stent body 52 spaced apart from the distal end may have more longitudinal and circumferential freedom of movement. For example, more proximal coils of stent body 52 are free to move longitudinally and circumferentially relative to one another and to cover 54. Some relative freedom of movement can allow the endoprosthesis to better navigate tortuous bends because the helical stent body and cover conform to small radius curves in the manner best suited to each.

Although cover 54 and stent body 52 are shown as being secured only at the distal end 77 of endoprosthesis 100, additional or alternative securing sites can be provided. For example, a cover and stent body can be secured at one or more proximally and/or centrally located securing sites. Each securing site can allow an amount of longitudinal and/or circumferential freedom of movement between the cover and stent body. In embodiments, a filament used to secure the cover and stent body is long enough to allow freedom of movement yet short enough to generally maintain the integrity of the endoprosthesis. Cover 54 includes a longitudinally extending slit or seam 110, at which opposed edges of the cover may meet or be joined. In some embodiments, the cover is formed in three dimensions without such a slit or seam.

Figure 3:
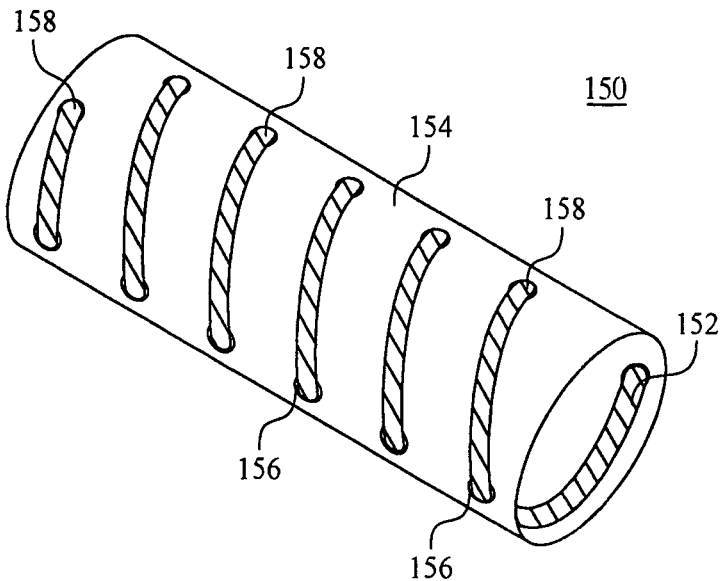
FIG. 3 is a perspective view of an endoprosthesis.

Referring to FIG. 3, an endoprosthesis 150 includes a stent body 152 threaded through entry fenestrations 156 and exit fenestrations 158 of a cover 154. The threading engagement can secure the stent body and cover without the need for additional securing elements, such as filaments. The threading engagement allows both circumferential and longitudinal freedom of movement between the stent body and cover. Circumferential or screw-like movement can occur when the stent body and cover rotate with respect to one another. Longitudinal movement along the major axis of the endoprosthesis can accompany the circumferential movement as some or all of the stent body threads through fenestrations 156,158.

Embodiments can include different configurations of fenestrations 156. For example, fenestrations 156,158 can be spaced apart by a plurality of coils along the longitudinal axis of the endoprosthesis. Accordingly, two or more adjacent coils can be interior (or exterior) to cover 154 before passing through another fenestration. This is an example of how cover 154 can be made to surround significantly more (or less) of the stent body than shown in FIG. 3. With respect to a length of the stent body, the ratio of the length internal to the cover to the length external to the cover may be between, e.g., about ⅕ and about 5. In embodiments, essentially all or all of the stent body is disposed within the cover. In other embodiments, essentially all or all of the stent body is disposed external to the cover.

Embodiments can include fenestrations disposed only at one or a few locations of the cover along a length of the endoprosthesis, e.g., at one or both ends or only centrally. For example, helical stent body 52 may pass through only a single centrally located pair of exit and entry fenestrations 156,158. Proximal and distal portions of the stent body may be located internal to or external to cover 154. These proximal and distal portions have significant freedom of movement with respect to cover 154.

In some embodiments, the fenestrations of the cover themselves have a different shape besides that shown. For example, the fenestrations may be elongated circumferentially and/or longitudinally with respect to the endoprosthesis. A fenestration elongated along a particular dimension can provide greater freedom of movement along the elongated dimension between the endoprosthesis and the stent body.

Figure 4A:
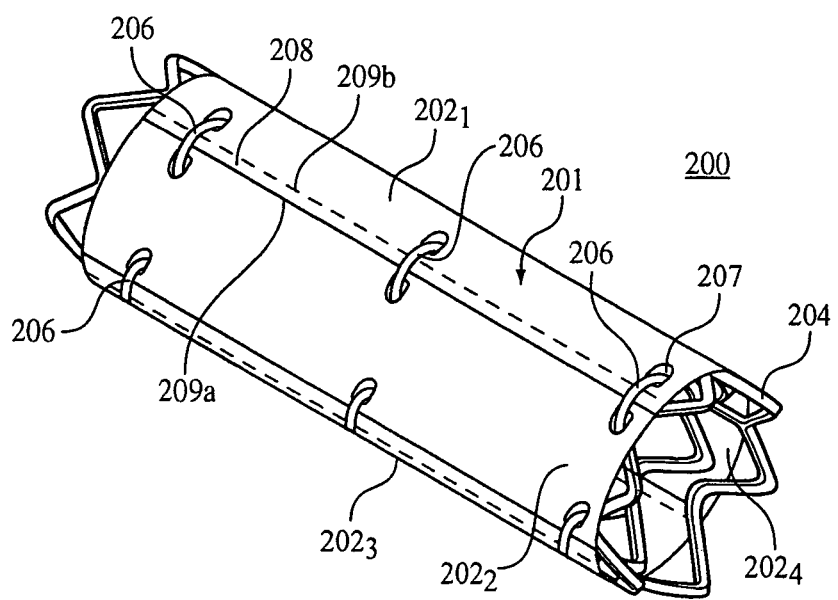
FIG. 4a is a perspective view of an endoprosthesis.
Figure 4B:
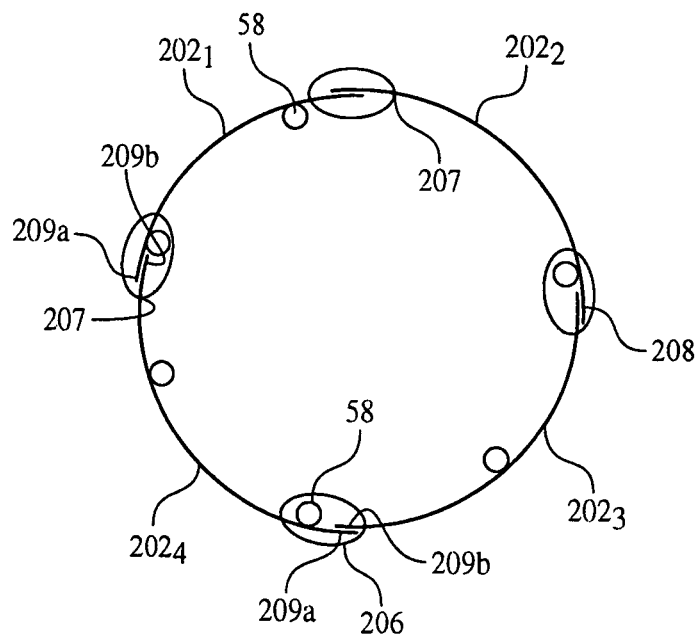

Referring to FIGS. 4a and 4b, an endoprosthesis 200 includes a cover 201 comprising a plurality of cover portions 202i. In the embodiment shown, the index i ranges from 1 to 4. FIG. 4b shows that a cross section of each individual cover portion taken perpendicular to a longitudinal axis of the endoprosthesis defines less than a complete circumference. Taken together, the cover portions 202i cooperate to define an essentially complete circumference that surrounds a stent body 204, which is shown as an open cell stent body but can include other types, e.g., closed cell, helical or mesh. Filaments 206 extend through fenestrations 207 of the cover and secure the adjacent cover portions together. As best seen in FIG. 4b, filaments 206 can also engage a framework member 58 of the stent body to secure the cover portions thereto.

Adjacent cover portions 202i have edges 209a, 209b that extend generally longitudinally with respect to the endoprosthesis. The edges of adjacent cover portions, e.g., portions 2022 and 2023, define a slit 208 extending longitudinally along the endoprosthesis. Slits 208 between adjacent cover portions 202i can have various configurations. As seen in FIG. 4b, the edges of adjacent cover portions overlap at slit 208. The extent of overlap between adjacent cover portions may be greater than that shown. In other embodiments, a slit is defined by the edges of adjacent cover portions that do not overlap and may even leave a gap between them. In some embodiments, a slit includes an edge of at least one of the cover portions folded about the edge of the other cover portion.

Whether or not the edges of adjacent cover portions overlap or included a folded about portion, adjacent cover portions have some degree of longitudinal and/or circumferential relative freedom of movement along at least a portion of the length of a slit. In some embodiments, relative freedom of movement is provided by not securing the adjacent edges of a slit for at least a portion of its length. For example, adjacent cover portions may be secured together at only one or a few longitudinal portions, e.g., at only a distal portion of the endoprosthesis. More proximal portions of the cover portions have greater freedom of movement. Fenestrations 207 can be elongated, e.g., circumferentially and/or longitudinally, to allow freedom of movement between adjacent cover portions.

Endoprosthesis 200 may also be provided with circumferential and/or longitudinal freedom of movement between one or more cover portions 202i and stent body 204. Filaments 206 can be long enough to allow such freedom of movement yet prevent complete separation of the cover portions and stent body. Relative freedom of movement along a particular dimension, e.g., circumferentially or longitudinally, may be provided by engaging filament 206 about framework members 58 generally aligned with the particular dimension so that cover portions 202i and stent body 204 can slide with respect to one another. The ability of the endoprosthesis to accommodate differential length changes can be enhanced by securing each cover portion to stent body 204 at substantially only one location along the length of the endoprosthesis.

When endoprosthesis 200 navigates a tortuous passage, each cover portion 202i can act like an individual strip rather than the cover 201 acting as a circumferential tube. Accordingly, cover 201 resists buckling even when navigating a small radius passage.

Slits 208 of endoprosthesis 200 are shown as extending linearly along a longitudinal axis of the endoprosthesis. Other longitudinally extending slits or seams can be used. For example, the slit or seams may extend both along a longitudinal and a circumferential dimension of the endoprosthesis, e.g., helically.

A length of a slit, e.g., a curved or helical slit, can be longer than a length of the cover. The length of such a slit can be determined as if straightened. In embodiments, a ratio of a length of one or more slits to a length of the cover is at least 0.1, at least 0.25, at least 0.5 at least 0.7, at least 0.9, or more. In embodiments, the ratio of the length of one or more slits to the length of the cover may be 1.5 or less, 1.25 or less, 1 or less, 0.9 or less, 0.75 or less, 0.5 or less, or 0.25 or less. In some embodiments, one or more slits extend to one or both ends of the cover.

In other embodiments, a deposited thin film having a plurality of cover portions is useable as an endoprosthesis without a supporting stent. For example, an endoprosthesis without a supporting stent can include a deposited thin film having one or more slits or seams extending generally along its length. One or both ends of the endoprosthesis may be a thicker deposited film than a central portion of the endoprosthesis.

Figure 5:
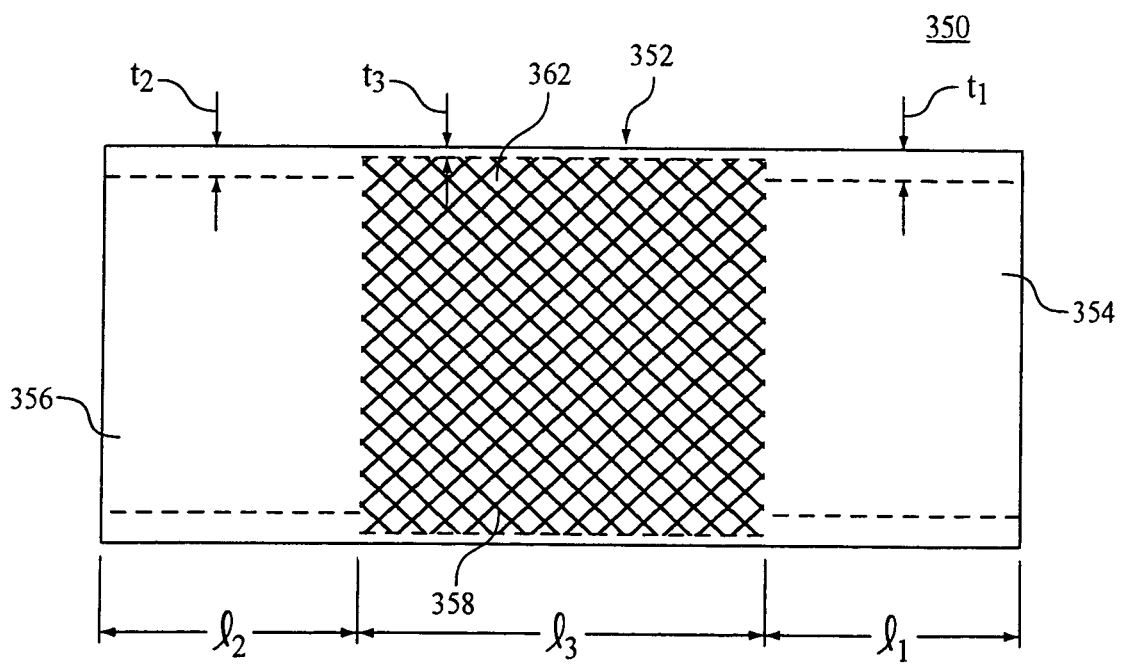
FIG. 5 is a side view of an endoprosthesis.

Referring to FIG. 5, an endoprosthesis 350 includes a metallic film 352 having first and second end portions 354, 356 and a longer central portion 358 having a plurality of fenestrations 362. The central and end portions have different mechanical properties that contribute to different aspects of the endoprosthesis functionality. End portions 354,356 have a respective length l1,l2 and a respective metallic film thickness t1,t2. Central portion 358 has a length l3, which is typically greater than one or both of l1,l2, and a thickness t3, which is generally less than one or both of t1,t2, The smaller thickness and fenestrations provide central portion 358 with a greater radial and longitudinal flexibility than end portions 354,356. Hence, the longer central portion flexes and conforms during radial compaction/expansion and delivery through tortuous pathways. End portions 354,356 are shorter than the central portion so that the end portions accommodate radial compaction/expansion and tortuous delivery without the need for substantial flexibility or conformability. Nonetheless, the end portions may have fenestrations or other features to impart a degree of flexibility.

Upon deployment at a treatment site, e.g., aneurysm 25, end portions 354,356 exert greater radial outward force than the central portion 358. Hence, the end portions secure the endoprosthesis with respect to a body passage to maintain alignment between the central portion and the treatment site. Typically, the central portion 358 provides an occlusive function with respect to a treatment site without exerting significant or even any radial outward force.

In some embodiments, a ratio of either or both of t1,t2 to t3 is at least 3, at least 5, or at least 10. In embodiments, either or both of t1,t2 may be at least 25 µm or at least 35 µm. Either or both of t1,t2 may be 75 µm or less or 50 µm or less. In embodiments, t3, may be 25 µm or less, 15 µm or less, or about 5 µm or less. The thicknesses t1,t2 may be different.

In embodiments, a ratio of 13 to either or both of 11,12 may be at least 2, at least 3, or at least 4. The lengths 11,12 may be different.

Endoprosthesis 350 can be manufactured by depositing a greater amount of metallic film at end portions 354,356 than central portion 358. Such deposition can be accomplished by photolithographic or mechanical masking of the central portion while depositing material over the end portions. Alternatively, or in addition, the end portions can include an integral substrate, e.g., a filament or stent body. The metallic film can be deposited over the integral substrate, which can provide additional mechanical toughness to the end portions. In some embodiments, however, the mechanical properties of the endoprosthesis result from the metallic film rather than a substrate, e.g., the endoprosthesis may not have a stent body or integral substrate.

Figure 6A:
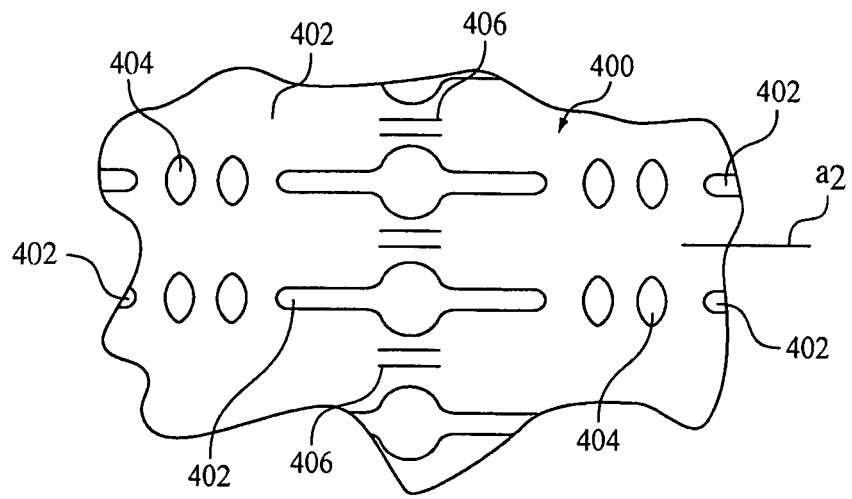
FIG. 6a is a top view of a portion of a metallic film suitable for use as a cover of an endoprosthesis. The metallic film is shown in a radially compacted state.
Figure 6B:
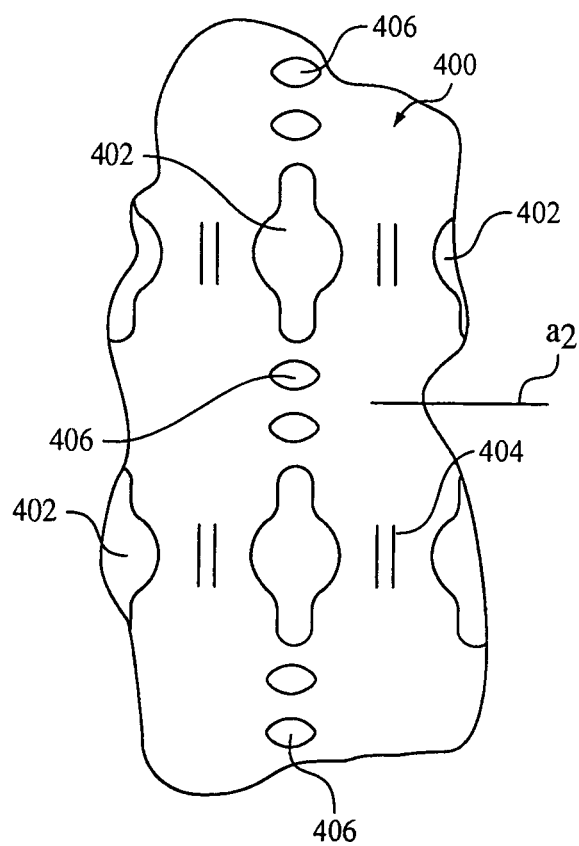
FIG. 6b is the metallic film of FIG. 6a in a radially expanded state.

Referring to FIGS. 6a and 6b, a metallic film 400 includes a pattern of fenestrations 402 and first and second sets of apertures 404,406. In a delivery device, the metallic film defines a generally tubular shape, which is compacted radially and is elongated with respect to a longitudinal axis of the film, e.g., generally parallel to a longitudinal axis of the delivery device. In the deployed state within a body passage, the metallic film defines a larger diameter tubular shape, being expanded radially and shortened with respect to the longitudinal axis of the film.

The configuration of the first and second sets of apertures enhances the ability of the metallic film to accommodate significant changes in length and circumference. Apertures 404,406 each define a respective major axis oriented at first and second different angles with respect to the longitudinal axis of the metallic film. For example, apertures 404,406 may be respectively oriented perpendicularly to and parallel to the longitudinal axis.

In the radially compacted state (FIG. 6a), apertures 406 are stretched along a small or zero angle with respect to the major axis of the apertures. Hence, apertures 406 may define slits aligned with the longitudinal axis $a_2$ in the radially compacted state, e.g., the apertures may be essentially closed. Apertures 404 are stretched at a non-zero angle with respect to the apertures. Hence, apertures 404 may define an opening spread apart along a dimension aligned with the longitudinal axis $a_2$. Fenestrations 402 are elongated generally parallel to the longitudinal axis.

In the radially expanded state (FIG. 6b), apertures 406 are stretched at a non-zero angle with respect to the apertures. Hence, apertures 406 may define an opening spread apart along a dimension perpendicular to the longitudinal axis $a_2$, e.g., an opening spread apart about a circumference of the metallic film. Apertures 404 are stretched along a small or zero angle with respect to the major axis of the apertures. Hence, apertures 404 may define slits perpendicular to the longitudinal axis $a_2$ in the radially expanded state, e.g., the apertures may be essentially closed. Fenestrations 402 are elongated generally perpendicularly to the longitudinal axis.

Figure 7:
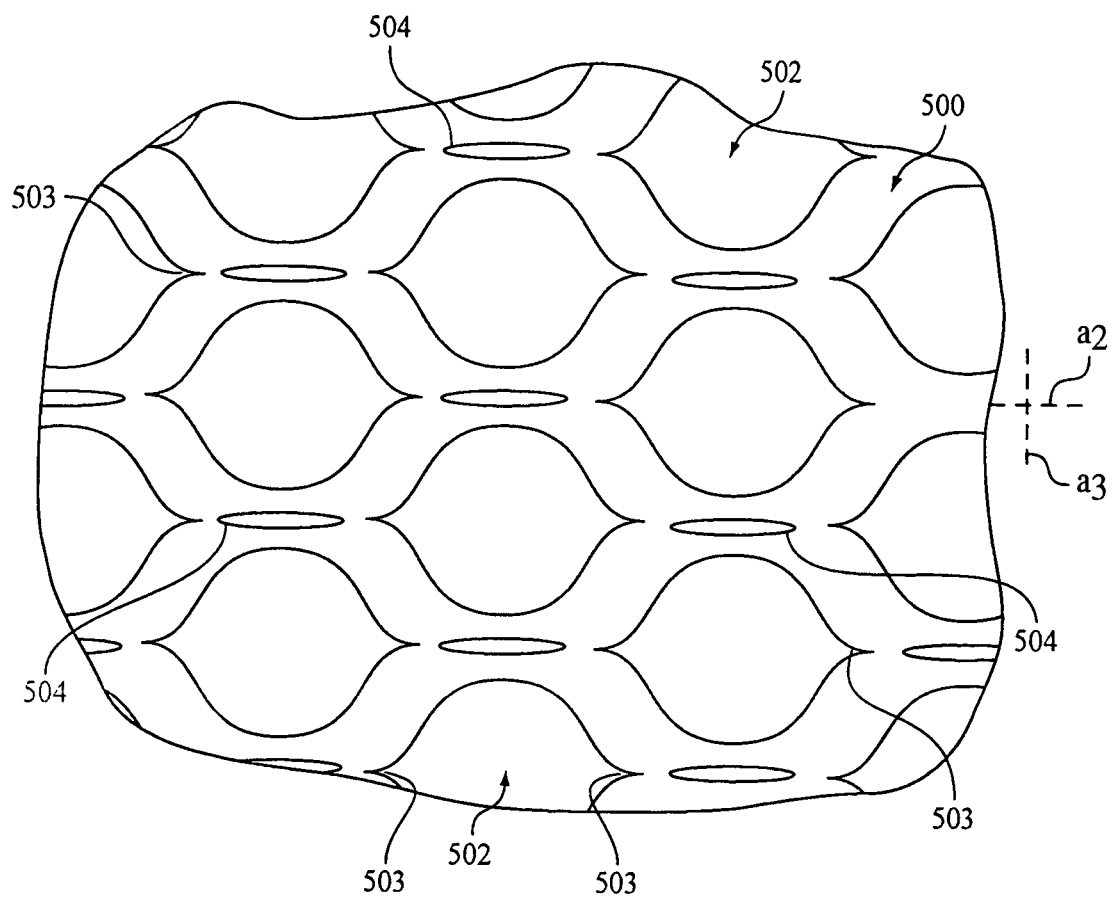
FIG. 7 is a top view of a portion of a metallic film suitable for use as a cover of an endoprosthesis. The metallic film is shown in a radially expanded state.

Referring to FIG. 7, a metallic film 500 includes a pattern of fenestrations 502 and apertures 504. Each fenestration 502 is spaced apart from adjacent fenestrations by an aperture 504, which allows the film to accommodate extra stress whether disposed internally or externally of a stent body. Apertures 504 are slits extending generally aligned parallel to longitudinal axis $a_2$ of an endoprosthesis including the cover. Consequently, apertures 504 may particularly open during excess radial expansion of the cover, which tends to stress the cover circumferentially, e.g., along an axis $a_3$ perpendicular to the longitudinal axis $a_2$.

Each fenestration 502 includes first and second apexes 503, which may be rounded internally. A line connecting the first and second apex 503 of each fenestration is generally parallel to longitudinal axis a2.

In embodiments shown, an endoprosthesis has a generally tubular shape. In some embodiments, however, the endoprosthesis (or a stent body or cover individually) has or includes other shapes such as conical, oblate, and branched. The endoprosthesis may have a closed end to form, e.g., a basket shape. Thin films, discussed above, composed of Ni—Ti-strength additive alloys and/or with modified microstructures, can be used in other applications. Examples include baskets, filters, catheters, guidewires, and medical balloons, such as an angioplasty balloon.

In embodiments, a metallic film is deposited on a substrate that includes or consists of a helical stent body. Hence, the metallic film and helical stent body are integral with one another.

Other examples of endoprostheses including a thin film as well as related systems and methods are described in U.S. provisional patent application No. 60/549,287, filed Mar. 2, 2004, which application is incorporated herein by reference.

An endoprosthesis may include a cover disposed externally to a framework as shown and/or internally of a framework. Endoprostheses having a cover including, e.g., a deposited thin film, disposed internally of a framework are described in U.S. patent application Ser. No. 11/025,464, titled MEDICAL DEVICES INCLUDING METALLIC FILMS AND METHODS FOR MAKING SAME, and filed concurrently herewith, which application is incorporated herein by reference.

The composition and/or fabrication method of a deposited thin film of an endoprosthesis may include features that enhance a strength or toughness of the film as described in U.S. patent application Ser. No. 11/025,860, titled MEDICAL DEVICES INCLUDING METALLIC FILMS AND METHODS FOR MAKING SAME, and filed concurrently herewith, which application is incorporated herein by reference.

An endoprosthesis may include a deposited thin film and a polymer as described in U.S. patent application Ser. No. 11/025,867, titled MEDICAL DEVICES INCLUDING METALLIC FILMS AND METHODS FOR MAKING SAME, and filed concurrently herewith, which application is incorporated herein by reference.

An endoprosthesis may include one or more filaments, e.g., wires, adapted to enhance mechanical properties of a deposited thin film as described in U.S. patent application Ser. No. 11/025,684, titled MEDICAL DEVICES INCLUDING METALLIC FILMS AND METHODS FOR MAKING SAME, and filed concurrently herewith, which application is incorporated herein by reference.

Methods for loading an endoprosthesis into a delivery device and systems for delivering an endoprosthesis to a treatment site are described in U.S. patent application Ser. No. 11/025,660, titled MEDICAL DEVICES INCLUDING METALLIC FILMS AND METHODS FOR LOADING AND DEPLOYING SAME, which application is incorporated herein by reference.

All publications, references, applications, and patents referred to herein are incorporated by reference in their entirety.

Other embodiments are within the claims.

What is claimed is:

1. An endoprosthesis defining a longitudinal axis and configured to have a radially compacted state within a delivery device and a radially expanded state when deployed within a body passage, the endoprosthesis comprising:

a metallic film having a thickness of about 50 μm or less, the metallic, film comprising a plurality of first apertures and a plurality of second apertures, the first and second apertures respectively oriented generally perpendicular to one another, wherein each first aperture is configured to (a) define an opening when the delivery device is in the radially compacted state and (b) define a substantially closed slit when the delivery device is in the radially expanded state, and wherein each second aperture is configured to (a) define a substantially closed slit when the delivery device is in the radially compacted state and (b) define an opening, when the delivery device is in the radially expanded state.

2. The endoprosthesis of claim 1, wherein the metallic film comprises nickel and titanium.

3. An endoprosthesis according to claim 1, wherein the metallic film comprises a tertiary alloy comprising nickel, titanium, and an additive in an amount between 0.2% and 20% by weight of the 4. An endoprosthesis according to claim 3, wherein the additive is chromium.

5. The endoprosthesis according to any claim 1, wherein the metal film is formed of a super-elastic or pseudo-elastic alloy.

6. An endoprosthesis according to claim 1, wherein the metallic film has a thickness of about 4 -35μm.

7. The endoprosthesis according to claim 1, further comprising radiopacity markers, 8. The endoprosthesis of claim 1, wherein the metallic film is deposited on a helical stent body.

9. The endoprosthesis of claim 1 wherein the endoprosthesis has a shape selected from: conical, oblate, branched, and having one closed end.

* * * * *